(12) United States Patent
Paltieli et al.

(10) Patent No.: US 6,626,832 B1
(45) Date of Patent: Sep. 30, 2003

(54) APPARATUS AND METHOD FOR DETECTING THE BENDING OF MEDICAL INVASIVE TOOLS IN MEDICAL INTERVENTIONS

(75) Inventors: Yoav Paltieli, Haifa (IL); Stuart Wolf, Yokneam (IL)

(73) Assignee: Ultraguide Ltd., Yokneam (IL)

(*) Notice: Subject to any disclaimer, the term of this patent is extended or adjusted under 35 U.S.C. 154(b) by 0 days.

(21) Appl. No.: 09/958,543

(22) PCT Filed: Apr. 16, 2000

(86) PCT No.: PCT/IL00/00224

§ 371 (c)(1),
(2), (4) Date: Jan. 7, 2002

(87) PCT Pub. No.: WO00/63658

PCT Pub. Date: Oct. 26, 2000

Related U.S. Application Data

(60) Provisional application No. 60/129,358, filed on Apr. 15, 1999.

(51) Int. Cl.[7] .................................................. A61B 8/00
(52) U.S. Cl. ........................ 600/439; 600/437; 128/897
(58) Field of Search ................................. 600/437, 443, 600/444, 427, 411, 461, 130, 459, 460, 439; 128/897–98; 351/41

(56) References Cited

U.S. PATENT DOCUMENTS

| | | | |
|---|---|---|---|
| 4,249,539 A | 2/1981 | Vilkomerson et al. | |
| 4,407,294 A | 10/1983 | Vilkomerson | |
| 5,095,910 A | 3/1992 | Powers | |
| 5,469,853 A | * 11/1995 | Law et al. | .................. 600/463 |
| 5,647,373 A | 7/1997 | Paltieli | |
| 5,724,978 A | 3/1998 | Tenhoff | |
| 5,829,444 A | * 11/1998 | Ferre et al. | .................. 128/897 |
| 5,957,844 A | 9/1999 | Dekel et al. | |
| 6,216,029 B1 | * 4/2001 | Paltieli | ........................ 600/427 |

FOREIGN PATENT DOCUMENTS

| | | |
|---|---|---|
| WO | WO 97/03609 | 2/1997 |
| WO | WO 99/27837 | 6/1999 |
| WO | WO 99/33394 | 7/1999 |

* cited by examiner

Primary Examiner—Francis J. Jaworski
Assistant Examiner—Maulin Patel
(74) Attorney, Agent, or Firm—Eitan, Pearl, Latzer & Cohen-Zedek

(57) ABSTRACT

An apparatus for detecting the bending of a medical invasive tool (2) during its insertion in a body (4, 6) comprises an ultrasound transducer (8), and a position measuring system (29, 22, 26, 28) including position measuring components, and/or articulated arms (20, 22) being attached to the medical invasive tool (2). The expected position of the medical invasive tool is calculated according to the measurements produced by the position measuring system. Echo points, and/or segments of the medical invasive tool are identified on the ultrasound image (24). The comparison between the identified echo, and the calculated position of the invasive tool (without bending) is the base of detecting the bending of the medical invasive tool. Additionally, the identified echo points/segments are used in order to evaluate the actual shape of the invasive tool. Additionally, the expected position, and/or velocity of the invasive tool calculated, and a representation thereof is displayed on the image of the invasive tool calculated, and a representation thereof is displayed on the image viewable to the user. Similar apparatus can be utilized when employing a CT scanner or MI scanner.

30 Claims, 6 Drawing Sheets

APPARATUS AND METHOD FOR DETECTING THE BENDING OF MEDICAL INVASIVE TOOLS IN MEDICAL INTERVENTIONS

CROSS REFERENCES TO RELATED PATENT APPLICATIONS

This PCT Patent Application is related to and claims priority from U.S. Provisional Patent Application No. 60/129,358, filed on Apr. 15, 1999, entitled: Apparatus And Method For Detecting The Bending Of Medical Invasive Tools In Medical Interventions, this Provisional Patent Application incorporated by reference in its entirety herein.

FIELD OF THE INVENTION

The present invention is related to the detection of medical invasive tool bending when inserted in a body, to evaluate its shape. It is also related to enhancing the ultrasound echo of an invasive tool.

BACKGROUND OF THE INVENTION

Imaging methods, such as ultrasound or CT are used to guide the insertion of surgical tools for diagnosis and therapy. For example, ultrasound imaging procedures are routinely performed in association with fetal monitoring and development, breast biopsy, other biopsies, aspirations and other intervention insertions.

Systems for performing guided medical invasive procedures are disclosed for example, in the commonly assigned U.S. Pat. No, 5,647,373 (Paltieli); and PCT Applications; PCT/IL96/00050 (WO 97/03609), entitled: Free-Hand Aiming Of A Needle Guide; and PCT/IL98/00578, entitled: System And Method For Guiding Movements Of A Device To A Target Particularly For Medical Applications, all tree documents being incorporated by reference in their entirety herein.

In these systems a medical invasive tool is guided to a target on a body viewed by a medical imaging device, such as an ultrasound, CT, MRI, etc. The guidance is based on the measurement produced by a position measuring system comprising position measuring components and/or articulated arms attached at known positions to the medical invasive tool and to the medical tool. If the medical invasive tool bends during its insertion its calculated position and trajectory may become incorrect. This may arise if the position measuring component(s) is (are) attached at a relatively far distance from the tip of the medical invasive tool. Placing the position sensor on the tip of the invasive tool may eliminate the problem. However, this generally requires dedicated tools and in most cases, still introduces errors regarding the expected trajectory of the tool.

Knowing the expected position and velocity of the invasive tool can also be used for enhancing the ultrasound echo of the invasive tool by applying image processing tools on the originally produced image.

U.S. Pat. No. 4,429,539 (Vilkomerson) presented a method and an apparatus for detecting the position of a needle under ultrasound by placing a transducer element on the skin and on the needle tip being cooperative.

U.S. Pat. No. 4,407,294 (Vilkomerson) presented a method and an apparatus for detecting the position of a needle tip under ultrasound comprising two ultrasound detectors on the needle, viewable when in the vicinity of the ultrasound beam. U.S. Pat. No. 5,095,910 (Powers) presented a method and an apparatus for detecting the needle tip under ultrasound comprising a movable part in the needle tip that elicits Doppler.

These methods enable the operator to position the needle tip when viewed by the scanning plane of an ultrasound device. However, they exhibit drawbacks in that they require dedicated tools. Additionally, these methods and apparatus for performing these methods cannot provide information about the amount of bending of the needle. Also, the method disclosed by Powers ('910) is compatible for Doppler ultrasound only.

SUMMARY OF THE INVENTION

The present invention improves the contemporary art by providing computer controlled method and apparatus for detecting the bending of a medical invasive tool during its insertion in a body. The present invention also discloses methods and apparatus that compensate for such bending if it occurs, and are useful for example in interventions under ultrasound, CT or MRI.

The present invention also provides methods and apparatus for enhancing the ultrasound echo of an invasive tool, therefore improving the quality of the ultrasound image.

The term "needle" is used herein to describe any invasive medical instrument or tool that is employed in a medical intervention. The term "position" will be used herein to describe location and/or orientation.

The term "position measuring system" is used herein to describe any system (magnetic, optic, acoustic, inertial, mechanical or any combinations thereof) that can be used in order to track the position of a body with respect to a reference position or with respect to another body in space. The term position measuring component is used to describe a component of a position measuring system, such as electro-magnetic/acoustic/optic transitter or receiver, reflector or other optic indicia, gyro or encoder, or any other component that enables the measurement of a body/set of coordinates with respect to another body/set of coordinates in space.

One embodiment of the apparatus of the present invention is semi-automatic, in that it requires the operator to maneuver the scanning head and/or the needle such as the scanning head views at least a portion of the needle or at least one point on the needle. The calculation of the expected needle position with respect to the scanning head and scanning beam is fully automatic, whereas recognizing the actual position of at least a portion of the needle on the image displayed by the medical scanning device may be automatic or manual.

The system comprises a medical imaging device, such as an ultrasound, a position measuring system comprising a position controller and position measuring components and/or articulated arms being attached to the needle and to the scanning head of the medical imaging device a dataprocessor, and an optional image processor. Additionally, the system comprises a display on which the operator can view the image produced by the imaging device and/or information regarding the position of the needle, and the amount of needle bending during insertion A first position measuring component is attached at a known position with respect to the needle and a second position measuring component is attached on the ultrasound transducer. The relative position between the first and second measuring component is measured by the position measuring system. The second position measuring component is calibrated to the ultrasound transducer such that the position of the scanning plane of the ultrasound is known with respect to the second position measuring component. The expected position of the needle with respect to the scanning plane/volume of the medical imaging device may then be calculated based on the measurements and calibration above. Alternately, the needle and/or the ultrasound transducer are placed on articulated arms enabling to measure their relative position by mechanical means (encoders).

The needle is aimed at a target in a body or body volume viewed by an ultrasound imaging system. If the needle is thin, it may bend during insertion. The transducer may then be maneuvered such as to view at least a portion of the needle or at least one point on the needle. Points and portions on the needle may be identified by automatically or semi-automatically procedures according to the ultrasound echo of the needle. The information received from the position measuring system (position and movement parameters) together with actual points detected from the ultrasound echo enables the evaluation of the shape of the needle, and particularly, needle bending.

Knowing the position and velocity of the needle is also used for enhancing the needle echo in an ultrasound image or set of images. Points on the needle are searched in the ultrasound image or set of ultrasound images, respectively, according to the expected position and velocity of the needle. Applying standard image processing tools such as interpolation functions and local sharpening filters enables them to enhance the complete needle echo based on the recognized point(s).

The current invention can improve the performance of medical guiding systems for medical intervention, such as for example, the guiding systems presented in commonly assigned U.S. Pat. No. 5,647,373 (Paltieli), PCT/IL96/00050 (WO 97/03609), entitled: Free-Hand Aiming Of A Needle Guide, and PCT/IL98/00578, entitled: System And Method For Guiding Movements Of A Device To A Target Particularly For Medical Applications, all three documents being incorporated by reference in their entirety herein, or other existing guiding systems. The improvement is particularly important in applications where the medical invasive tool is thin and the position measuring component attached to the needle is not on the tip of the needle.

BRIEF DESCRIPTION OF THE DRAWINGS

The invention will now be described with reference to the accompanying drawings, where like reference numerals or characters indicate corresponding or like components. In the drawings.

DETACHED DESCRIPTION OF THE DRAWINGS

Figure 1:
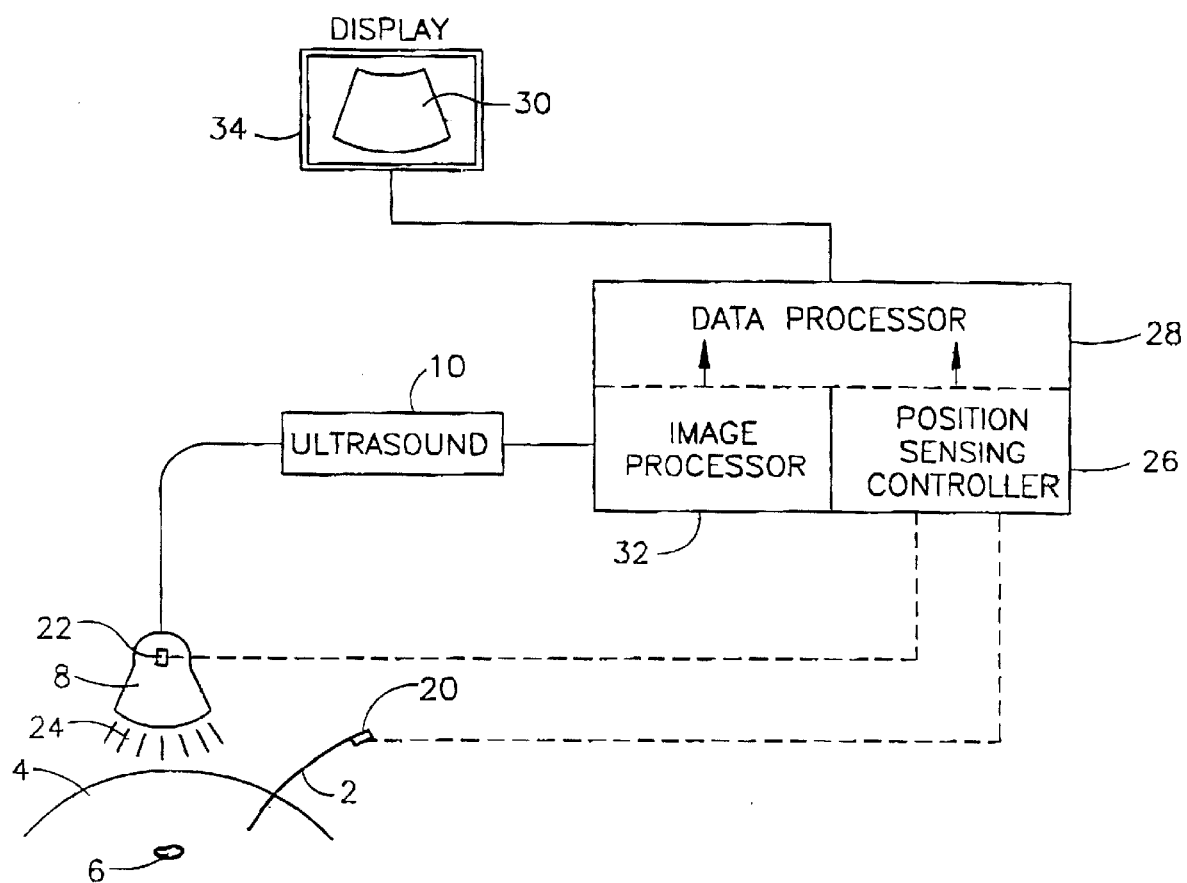
FIG. 1 pictorially illustrates one form of a system constructed in accordance with an embodiment of the present invention for detecting the bending of a needle when inserted in a body by using an ultrasound.

Reference is now made to FIG. 1 that illustrates a first embodiment of the present invention. The first embodiment illustrates a biopsy needle 2 inserted in a body 4 (or body volume) comprising a target 6. The target 6 is scanned by an ultrasound transducer 8 connected to an ultrasound main unit 10. A first position measuring component 20 (p.m.c. or p.m.c._20 in the equation below) is attached at a known position onto needle 2. A second position measuring component 22 (p.m.c. or p.m.c._22 in the equation below) is attached at a known position with respect to ultrasound transducer 8. The second position measuring component 22 being calibrated to the ultrasound plane/volume 24, such that the position of the ultrasound plane/volume 24 is known with respect to second position measuring component 22. Such calibration can be achieved by opening according to the commonly assigned PCT application PCT/IL98/00631, entitled: Calibration Method And Apparatus For Calibrating Position Sensors On Scanning Transducers, incorporated by reference in its entirety herein.

The first position measuring component 20 and the second position measuring component 22 are part of a position measuring system additionally comprising a position sensing controller 26 which measures the relative position between them and transfers it to a data processor 28. Optionally, position sensing controller 26 can be part of the data processor 28.

Data processor 28 calculates the expected position of the needle 2 with respect to ultrasound scanning plane/volume 24. This calculation is based on the measurements produced by position measuring system on the knowledge of the shape of needle 2 and the position of said first position measuring component 20 on needle 2. Additionally, this calculation is based on calibration values related to the position of ultrasound scanning plane/volume 24 with respect to the second position measuring component 22. Such guiding systems employed here are according to the commonly assigned PCT applications PCT/IL96/00050 (WO 97/03609), entitled: Free-Hand Aiming Of A Needle Guide; and PCT/IL98/00578, entitled: System And Method For Guiding Movements Of A Device To A Target Particularly For Medical Applications; and U.S. Pat. No. 5,647,373 (Paltieli), all three of these documents incorporated by reference in their entirety herein.

The above calculation may be altered in case the needle 2 bends during its insertion in the body 4, as illustrated in FIG. 1, and in particular, if the position measuring component 20 is placed at a distance from needle tip. It is therefore, necessary in such cases to identify needle bending and compensate the calculations accordingly and/or issue information regarding the bending to the operator.

Figure 2A:
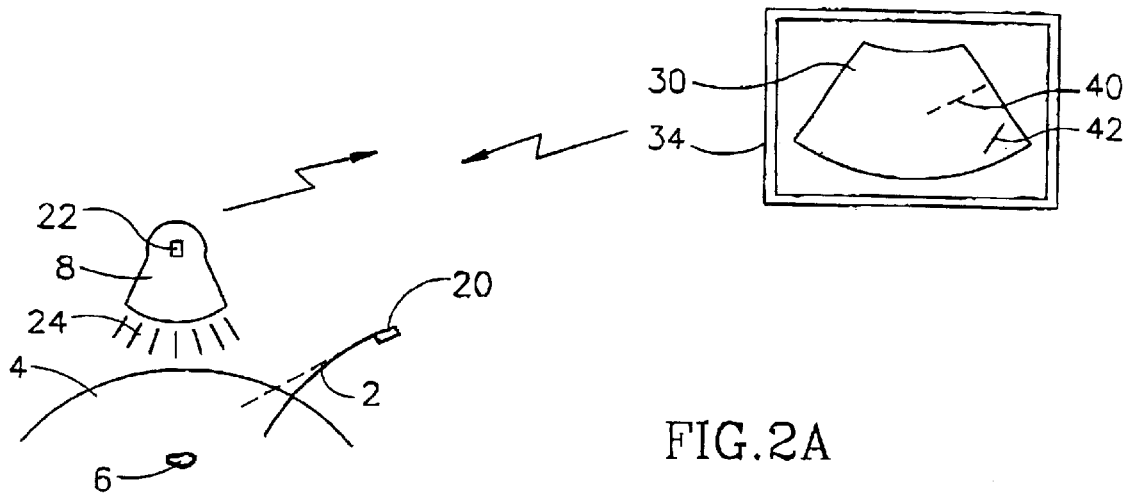
FIG. 2a pictorially illustrates the relationship between the bent needle and the straight needle in the body and on a display in relation to FIG. 1.

With reference to FIG. 2a, according to one embodiment of the present invention, ultrasound image 30 is transferred to an image processor 32 and then can be seen by the operator on a display 34. With reference to FIG. 2a and according to commonly assigned PCT Patent Applications, PCT/IL96/00050 and PCT/IL98/00578, and U.S. Pat. No. 5,647,373, the expected position of the needle 2 may also be superimposed on the ultrasound image 30. Optionally, the image processor 32 can be part of the data processor 28.

In order to check whether the needle 2 maintains its shape, ultrasound transducer 8 scans at least a portion of body 4 comprising a portion or at least a point of needle 2. The operator may be assisted in positioning the ultrasound, so as to view at least a point of the needle 2, by information displayed on the display 34 regarding the relative position between the needle 2 and the ultrasound plane 24.

The operator can therefore see on the display 34 needle echo points and/or segments. According to one embodiment of the present invention, the operator may then indicate on ultrasound image 30 the actual position of needle echo 42 for example, by placing a cursor on said needle echo points and clicking a button with the help of a mouse and standard software. The operator performs this operation in one or several ultrasound images.

Image processor 32 may then calculate the two dimensional (2D) positions of the marked points in the image with respect to ultrasound image 30. Since the second position measuring component 22 is calibrated to ultrasound plane/volume 24 the position of the marked points may then be calculated with respect to the second position measuring component 22. The position of the marked points may then be calculated with respect to the first position measuring component 20 according to the following equation:

$$P_{point}^{p.m.c\_20} = P_{p.m.c\_22}^{p.m.c\_20} + [M_{p.m.c\_20}^{p.m.c\_22}] * P_{point}^{p.m.c\_22}$$

where P stands for displacement vector, [M] stands for Euler orientation matrix, the lower index stands for the point that is measured and the upper index stands for the coordinate set to which it is measured.

Data processor 28 has therefore information regarding the actual position of points on needle 2 with respect to position measuring component 20 $\{P_{points\_i}^{p.m.c\_20}\}_{ie\ \{t,k\}}$ where K is the number of marked points according to ultrasound image 30. Data processor 28 then performs the task of fitting a curve through this set of points in order to evaluate the shape of needle 2.

Figure 2B:
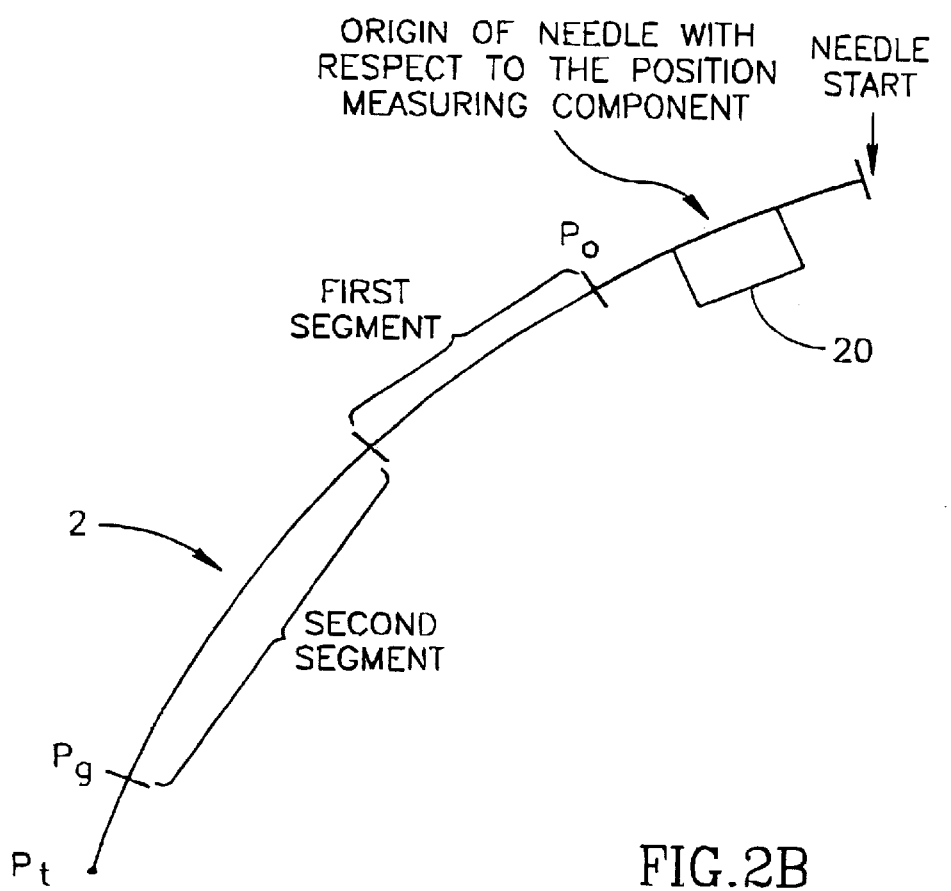
FIG. 2b pictorially illustrates possible partitioning of a bent needle suitable for performing curve fitting according to the methods introduced in the present invention.

If the relative position between the ultrasound transducer 8 and the needle 2 enables the positioning of at least a portion of needle 2 in the ultrasound scanning plane 24, as illustrated in FIG. 2b, several points on the needle 2 may be detected from its echo in one image. The detected points may be arranged in a suitable cluster and points which cannot be fitted to the cluster may be rejected. If, however, needle 2 is crossing said ultrasound scanning plane 24 a single crossing point may be detected from one position. In this case it is preferable to maneuver the ultrasound transducer 8 at several positions in order to view several points on needle 2. Optionally, but highly preferred, the operator should view and mark the needle tip. Knowledge of the actual needle tip position simplifies and may improve the performance of the selected curve fitting model/algorithm (detailed below).

Figure 2C:
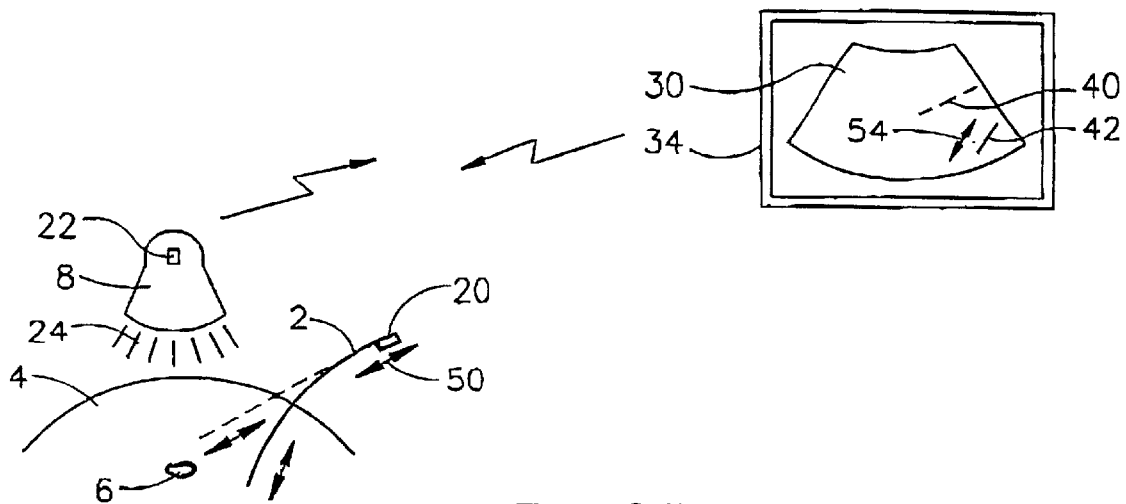
FIG. 2c pictorially illustrates the option of moving cooperatively the needle in order to enable automatic detection of the needle ultrasound echo.

Also optionally, but highly preferred, additional values may be used in such algorithms, detailed below, and as further explained in relation to FIG. 2c. A first value is related to a predetermined point(s) $P_o$ whose position with respect to position measuring component 20 cannot be changed by bending. A second value relates a predefined point(s) $P_r$ whose position with respect to needle tip $P_t$ cannot be changed by bending. These predefined values may be predefined according to information regarding the size and nature of needle 2 and the nature of the attachment of position measuring component 20 to needle 2.

The curve fitting scheme used by the algorithm, may be either an interpolation scheme where the curve must pass through the points or an approximation scheme where the curve does not necessarily pass though all the points. In the latter case error criterions such as maximum error or integral square error may be used in order to automatically define the measure of closeness of the approximation.

The estimation of needle shape may be performed according to any of many possible curve fitting models known in the art. Polynomial interpolation, Bezier polynomials, curve fitting with B-splines (interpolation or approximation) are some conventional algorithms that can be used for evaluating the shape of the needle 2, based on its echo and the information provided by the position measuring system.

Optionally, but preferred, is that the needle may be divided into several segments, and that the cure fitting algorithm model is performed according to the assumption that the bending is different in the different needle segments. Optionally, but preferred, estimations regarding the smoothness of the approximation should be used in order to improve the performance of the curve fitting algorithm. Such estimations should be performed according to empirical data. Optionally, different bending models could be fitted to different types of invasive tools according to the nature and size of different needles, again according to empirical data.

According to another embodiment of the present invention the detection of the needle echo may be performed automatically, therefore releasing the operator of the task of marking the needle echo 42 on display 34. With reference to FIG. 2c, the operator moves needle 2 in a cooperative mode for example by a back and forth oscillation 50 while holding ultrasound transducer 8 still (or almost still). The cooperative movement enables the image processor 32 to automatically detect actual needle echo 42 on the ultrasound image 30 based on the movement of needle echo 54. The automatic detection is based on the information regarding position and movement of the needle 2 (frequency, amplitude) according to following scheme.

The first position measurement component 20 enables measurement of the position of needle 2. When needle 2 is moved in a cooperative mode by the operator the frequency, direction and amplitude of the movement may be calculated according to the position measurements. If the needle 2 bends, the measured direction of the movement is dependent on the location of the first position measuring component 20 on needle 2.

Image processor 32 analyzes successive ultrasound images 30, by evaluating moving points in the image. This evaluation is assisted by information received from data processor 28 regarding measured parameters characterizing the movement of the needle 2, its frequency and/or amplitude and/or direction. The calculated frequency and amplitude are the preferred parameters for the search since if needle 2 bends during its insertion, movement direction of needle echo 54 is different from calculated movement direction 50. Image processor 32 then filters the successive images in search for points moving according to the measured parameters.

Additionally, in an ultrasound apparatus having Doppler capability, the automatic recognition of the actual needle echo may be assisted by the additional information produced by the ultrasound apparatus regarding moving objects in a image.

The necessary number (amount) of consecutive ultrasound images for automatically detecting needle points based on its cooperative movement is dependent on the nature of the movement and on the amount of the needle 2 that is viewable (on the display 34). Confining the automatic search for needle echo points around the expected (without bending) needle trajectory 40 improves performance and speeds up the recognition process.

Optionally, but preferred, the operator should view the needle tip in order to facilitate the automatic target recognition process.

Figure 2D:
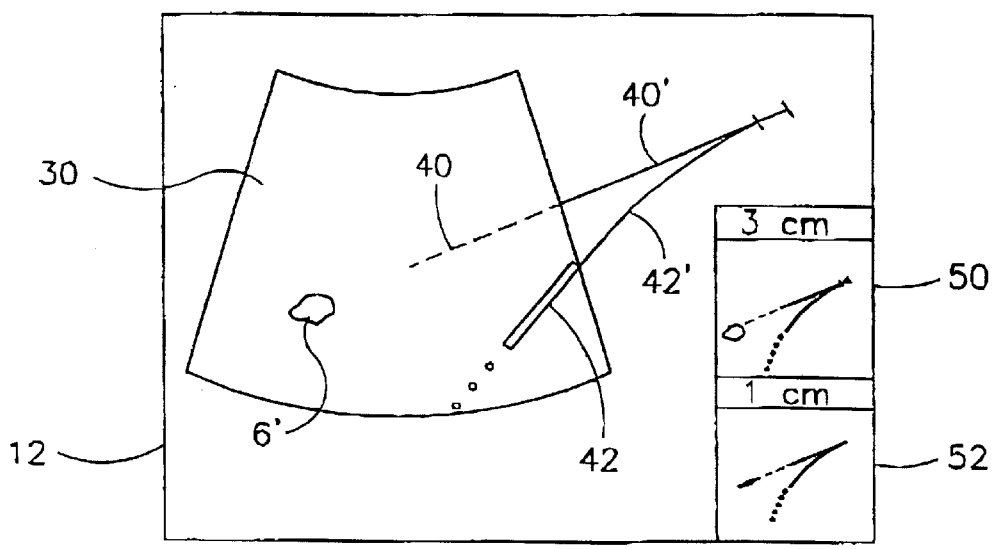
FIG. 2d pictorially illustrates possible display of relationships between the actual bent needle and the expected straight needle in relation to FIG. 1.

FIG. 2d illustrates several options of showing to the operator information regarding the bending of needle 2 on the display 34. One option is to indicate the actual needle echo 42 versus the expected needle echo 40 on ultrasound image 30. Additionally, a continuation of actual needle echo 42' and a continuation of expected needle echo 40' can be indicated. Additionally, a representation of the expected trajectory based on the evaluation of the needle bending can be displayed on ultrasound image 30. Additionally, the 2D topview 50 and 2D side-view 52 images of needle bending versus straight needle may be displayed together with numerical information, for example alphanumeric information regarding the distance between the actual needle tip and the expected (no bending) needle tip.

In a intervention guiding system, such as those introduced in PCT/IL96/00050, the PCT/IL98/00578 and U.S. Pat. No. 5,647,373, the direction and position of the invasive tool to be guided may be updated according to the evaluated shape of said invasive tool. This approximation can be later changed according to whether the operator chooses to proceed or to withdraw said invasive tool. Additionally, an alarm may be issued to the operator if the amount of estimated bending causes an expected deflection from the desired hit point larger than a predefined amount. Still additionally, if target 6 is indicated in body 4, for example by methods described in the above cited PCT/IL96/00050, PCT/IL98/00578 and U.S. Pat. No. 5,647,373, data processor 28 may estimate the miss distance caused by the bending and display this information to the operator and/or issue an alarm if this miss distance is above a certain threshold.

Figure 3:
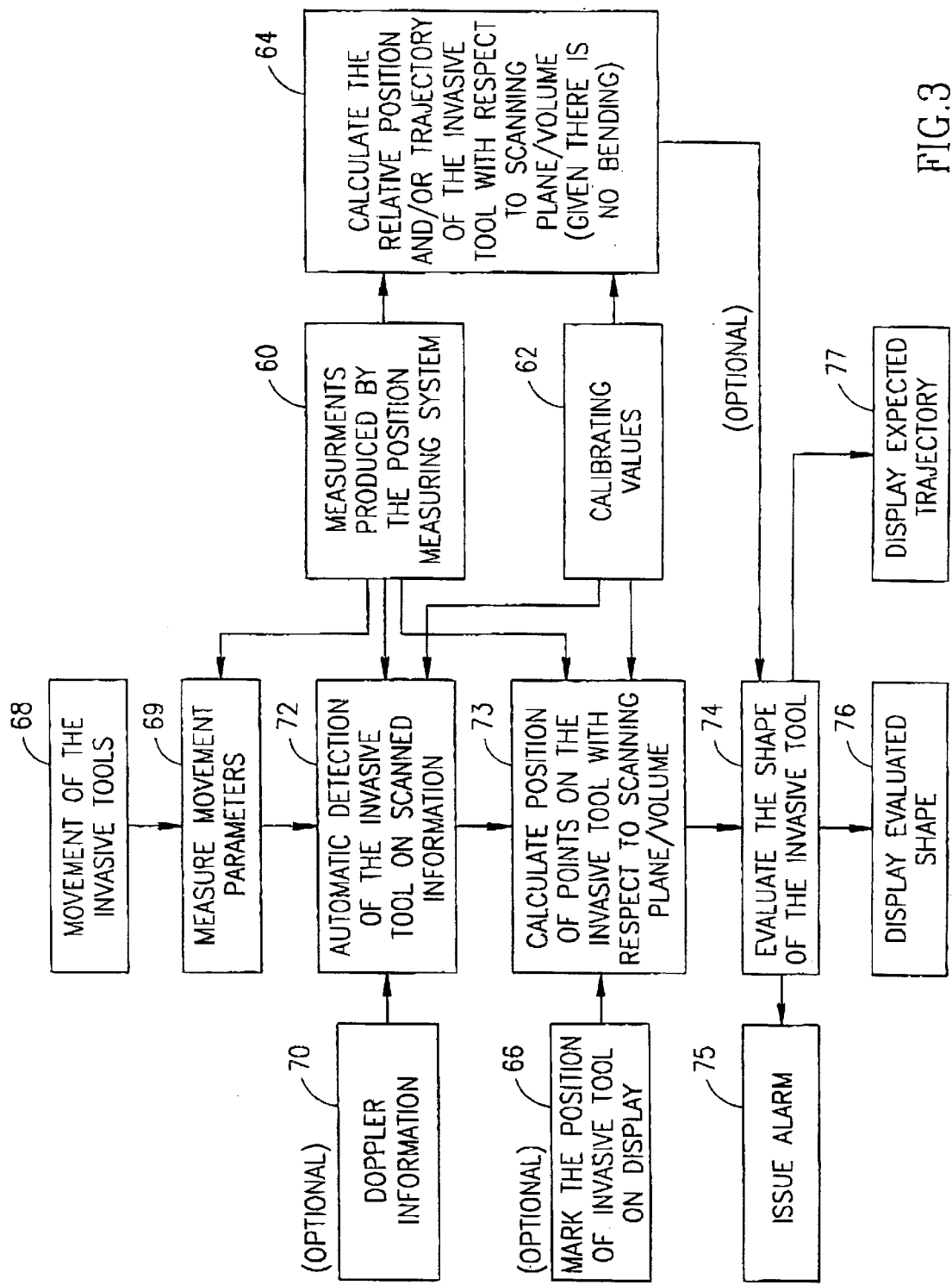
FIG. 3 is a block diagram illustrating the steps involved in calculating the amount of bending in relation to FIG. 1.

Referring to FIG. 3, block 60 shows the measurements produced by the position measuring system. Block 62 shows the result of the calibrating position measuring component 22 to ultrasound transducer 8. Block 62 is performed off-line Block 64 shows the calculation of the relative position of needle 2 with respect to ultrasound scanning plane 24. Block 66 describes the option of marking the acts position of points of needle 2 on its displayed image according to the image produced by said ultrasound. Block 68 describes the movement of needle 2. Block 69 shows the optional step of measuring the movement parameters (frequency, amplitude, direction) based on the measurements produced at step 60.

Block 70 describes the option of receiving Doppler information from ultrasound Block 72 describes the option of automatically detecting points on the needle 2 on scanned information, based on Doppler information step 70 (optional), movement parameters step 69, and/or measurements produced at step 60, and calibrating values at step 62. Block 73 describes the step of calculating the position of points on the invasive tool with respect to scanning plane/volume 24 based either on step 66 or on step 72 and employing measurements at step 60 and calibration values from step 62. Block 74 describes the step of evaluating the shape of the invasive tool based on the calculations at step 73 and optionally on the calculations at step 64. Block 75 describes the step of issuing an alarm if the bending is beyond a certain level, based on the evaluation at step 74. Block 76 describes the step of displaying the evaluated shape of the invasive tool. Block 77 describes the step of displaying the expected trajectory of the invasive tool based on the evaluated shape from step 74.

Figure 4A:
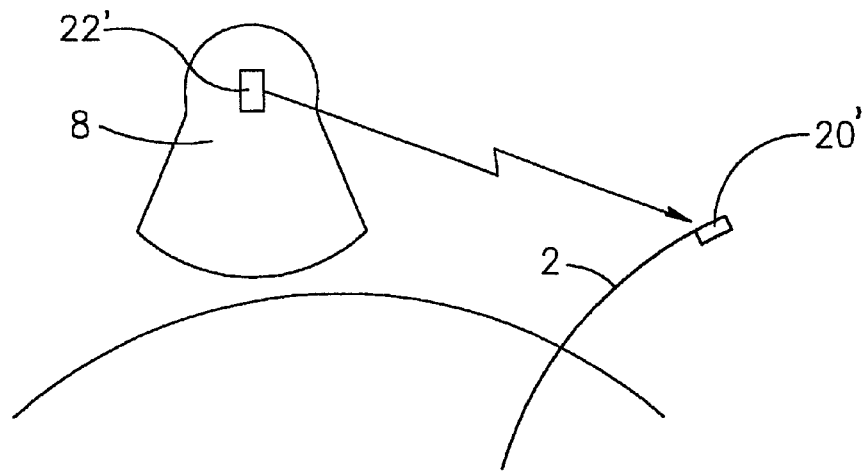
FIG. 4a pictorially illustrates one possible position measuring system to be used in accordance with an embodiment of the present invention.

Reference is now made to FIG. 4a that illustrates a magnetic position measuring system to be used in accordance with an exemplary embodiment of the present invention. Similar items in previous figures have similar numbers and will not be further described.

In this exemplary embodiment, the first position measuring component 20 is a receiver 20' being attached to needle 2 and position measuring component 22 is a transmitter 22' being attached to ultrasound transducer 8. Transmitter 22' is transmitting AC or DC magnetic/electromagnetic signals to receiver 20'. The output of receiver 20' is transmitted by wire or wireless connection to position sensing controller 26 enabling to calculate the relative position of receiver 20' with respect to transmitter 22'. Alternately, position measuring component 20 could be a transmitter and position measuring component 22 could be a receiver.

Figure 4B:
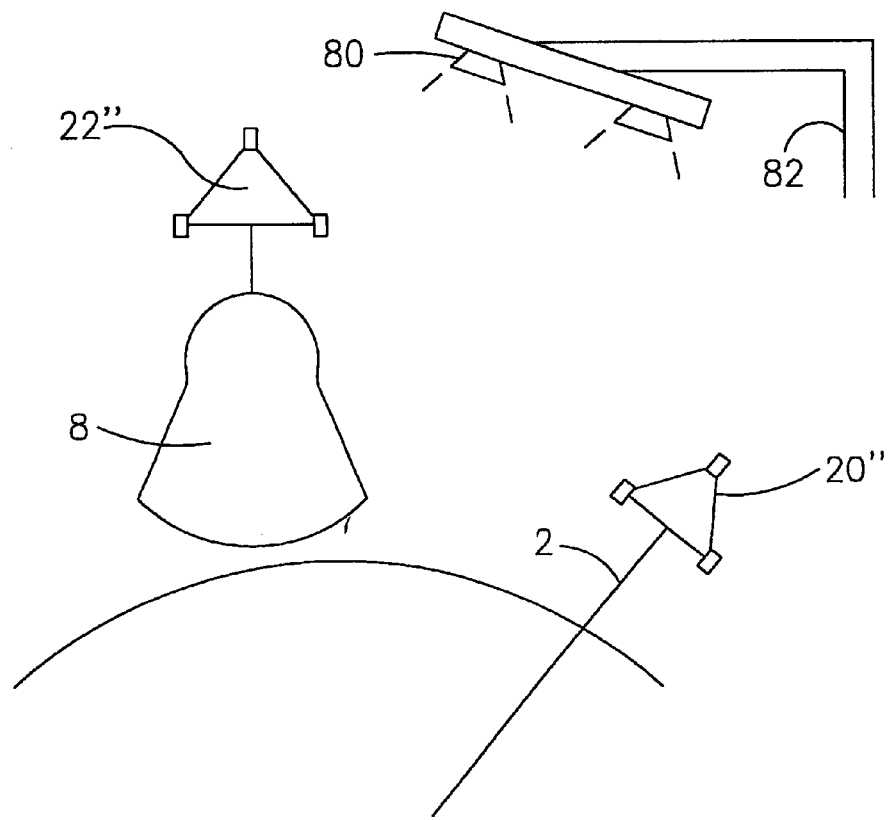
FIG. 4b pictorially illustrates another possible position measuring system to be used in accordance with an embodiment of the present invention.

Reference is now made to FIG. 4b wherein an optical position measuring system is employed in accordance with another exemplary embodiment of the present invention. Similar items in previous figures have similar numbers and will not be further described.

A stereo vision CCD 80' is positioned on an arm 82' at a first reference location. The first position measuring component 20 includes a cluster of LED's 20" being attached to needle 2 and said second position measuring component 22 includes a cluster of LED's 22" being attached to ultrasound transducer 8. The relative position of cluster of LED's 20" is measured with respect to said first reference location (said stereo CCD camera 80'), and also the relative position of cluster of LED's 22" is measured with respect to said first reference location (stereo CCD camera 80'). It is therefore possible to calculate from the above measurements the relative position of cluster of LED's 20" with respect to cluster of LED's 22" and hence, the relative position of the needle 2 with respect to the ultrasound scanning beam 24.

Figure 4C:
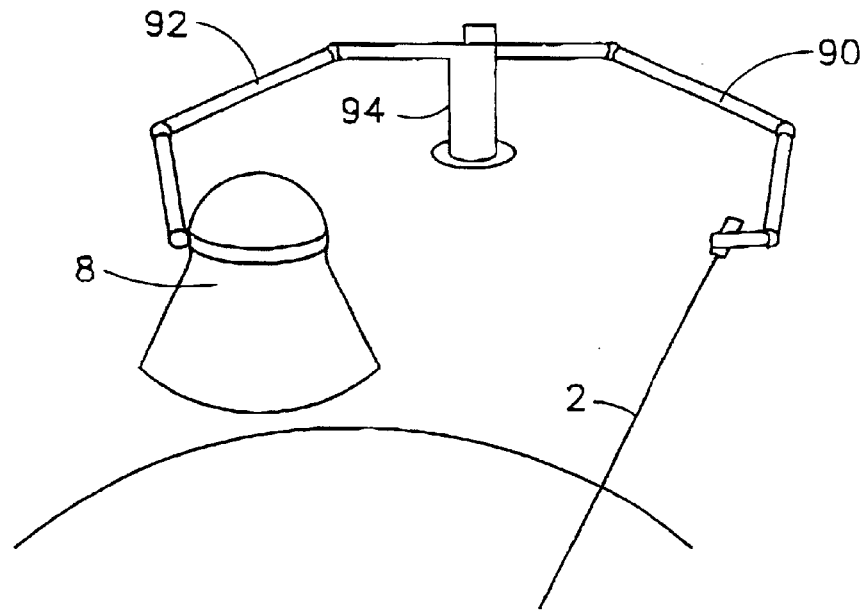
FIG. 4c pictorially illustrates one possible position measuring system to be used in accordance with an embodiment of the present invention.

Reference is now made to FIG. 4c wherein a mechanical position measuring system is employed in accordance with another exemplary embodiment of the present invention. Similar items in previous figures have similar numbers and will not be further described.

An articulated arm 90 is attached at a known position to needle 2 and a similar articulated arm 92 is attached at a known position to ultrasound transducer 8. Articulated arms 90 and 92 are placed on a common base 94. Such a system was introduced in U.S. Pat. No. 5,647,373. The mechanical position measuring system enables the calculation of the relative position of the needle 2 with respect to the ultrasound scanning plane 24.

Figure 4D:
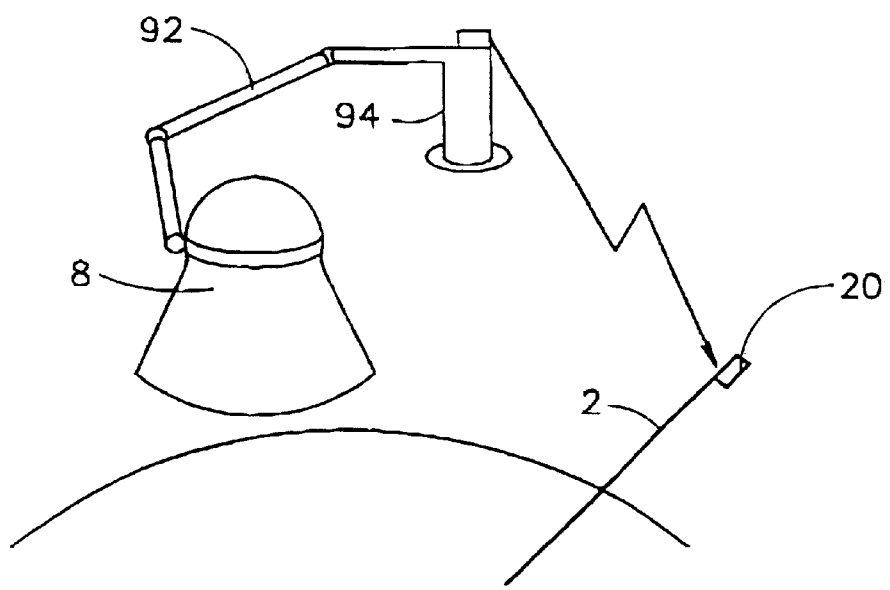
FIG. 4d pictorially illustrates another possible position measuring system to be used in accordance with an embodiment of the present invention.

Reference is now made to FIG. 4d wherein a combined magnetic—mechanical position measuring system is employed in accordance with another exemplary embodiment of the present invention. Similar items in previous figures have similar numbers and will not be further described.

An articulated arm 92 is attached at a known position to ultrasound transducer 8. A magnetic transmitter is positioned either on arm 92 or on base 94 and it is calibrated to articulated arm at a known position to ultrasound transducer 8. Articulated arms 90 and 92 are placed on a common base 94. Such a system was introduced in PCT/IL98/00578. The mechanical position measuring system enables calculation of the relative position of the needle 2 with respect to the ultrasound scanning plane 24.

Position measuring components 20, 22 and 80 (if included in the system) may be any of the following group: transmitter or receiver or reflector or transceiver or optical indicia or any combination of the above, suitable to be part of a magnetic, acoustic or optic position measuring system, these position measuring components and systems, for example, as detailed in PCT/IL96/00050, PCT/IL98/00578 and PCT/IL98/00631. The position sensing controller may communicate with at least one or all of position measuring components 20, 22 and 80 (if included in the system) by wired or wireless links (also as detailed for example in PCT/IL96/00050, PCT/IL98/00578 and PCT/IL98/00631).

According to additional aspects of the present invention, the position and/or the velocity of the needle is measured as described above. These measurements are used for automatically recognizing needle echo points or needle echo segments in the image or series of images produced by the ultrasound. Based on the above recognition, data processor 28 then applies standard image processing algorithms for filtering the ultrasound image, and enhances the needle echo in the image displayed to the user. Particularly, local sharpening filters and interpolation algorithms as detailed above can be used for creating a better ultrasound image to the user. Still alternately, measuring the position and the velocity of the needle is used for applying local filters on the ultrasound image in the area where the needle is expected. In this implementation, this is performed without first recognizing needle echo points or needle echo segments and by using generic filters. The parameters of the generic filters are preferably selected by the data processor 28 according to the type of ultrasound and according to the expected orientation of the needle in the image. Iterative or adaptive filtering algorithms can also be implemented on series of images in order to improve the resulting needle echo in the displayed image.

The enhancement of the ultrasound image is particularly useful in applications where needles are inserted at larger depths and at steep angles. The display may be in the standard form of ultrasound images or coloring schemes may be used to enhance the needle echo in the displayed image. The coloring schemes may be, for example, similar to Doppler colors used in Doppler ultrasounds.

While the invention has been described with respect to several preferred embodiments, it will be appreciated that these are set forth merely for purposes of example, and that many variations, modifications and applications of the invention may be made. Accordingly, the scope of the invention is defined by the claims which follow.

What is claimed is:

1. A method for detecting the bending of an medical invasive tool during its insertion in a body, the method comprising the steps of:
   scanning said body by an ultrasound transducer so a to view at least a portion of said medical invasive tool;
   calculating the position of said medical invasive tool with respect to said ultrasound transducer by means of a position measuring system comprising at least one of position measuring components or articulated arms being at known positions with respect to both of said medical invasive tool and said ultrasound transducer;
   identifying at least one of echo points or echo segments of said medical invasive tool according to the image produced by said ultrasound;
   comparing the position of said identified at least one of said echo points or said echo segments with an expected position; and
   calculating the position of said at least one of said echo points or said echo segments with respect to a position measuring component attached to said invasive tool and evaluating the shape of said invasive tool based on said calculation.

2. The method of claim 1, wherein said identification of said echo is performed in a single ultrasound image.

3. The method of claim 1, wherein said identification of said echo is performed in multiple ultrasound images.

4. The method of claim 1, wherein said identification of said echo include employing Doppler information received from said ultrasound.

5. The method of claim 1, wherein said identification of said echo is performed by marking the echo of said medical invasive tool as produced by said ultrasound on a display.

6. The method of claim 1, wherein said identification of said echo is performed automatically from the image produced by said ultrasound.

7. The method of claim 6, wherein said automatic identification is assisted by the relative movement of the invasive tool with respect to said ultrasound transducer.

8. The method of claim 7, wherein the expected movement of the invasive tool is calculated and then used in order to facilitate said automatic identification.

9. The method of claim 1, wherein said medical invasive tool is a biopsy needle.

10. The method of claim 1, additionally comprising the step of displaying, a representation of the shape of said invasive tool in the form of at least one of alphanumeric information or graphic information overlaid on the image produced by said ultrasound.

11. The method of claim 1, additionally comprising the step of projecting and displaying the expected trajectory of said medical invasive tool according to its bending.

12. The method of claim 1, wherein said step of calculating the position of said medical invasive tool with respect to said ultrasound transducer is based on at least one direct measurement.

13. The method of claim 1, wherein said step of calculating the position of said medical invasive tool with respect to said ultrasound transducer is based on first measuring the position of said medical invasive tool and said ultrasound transducer with respect to a reference position.

14. The method of claim 1, additionally comprising the step of enhancing the echo of said invasive tool in the image displayed to the user.

15. The method of claim 14, wherein said enhancement is based on said identification of echo points or echo segments.

16. The method of claim 14, wherein said enhancement is based on said calculation of the relative position or velocity of said invasive tool with respect to said ultrasound transducer and applying generic local image processing tools on the image produced by said ultrasound, and without using any said identified echo points or echo segments.

17. Apparatus for detecting the bending of a medical invasive tool during its insertion in a body, the apparatus comprising:
   an ultrasound transducer for scanning a body so as to view at least a portion of said medical invasive tool;
   a position measuring system comprising a position sensing controller, at least one of at least one position measuring component or an articulated arm being at a known position with respect to said medical invasive tool, and said at least one of said at least one position measuring component or said articulated arm being at a known position with respect to said ultrasound transducer;

a data processor for receiving data from said position sensing controller for calculating the relative position of said medical invasive tool to said ultrasound transducer, said data processor programmed for:
  identifying on the image produced by said ultrasound the echo points or echo segments of said medical invasive tool;
  comparing the position of at least one of said identified echo points or echo segments of said medical imaging device with said calculated relative position; and
  based on said comparison evaluating the amount of bending of said medical invasive tool during its insertion in said body; and
  calculating the position of said at least one of said echo points or segments with respect to a position measuring component attached to said invasive tool; and
  evaluating the shape of said invasive tool based on said calculation.

18. The apparatus of claim 17, wherein said data processor is additionally programmed to display a representation of the shape of said invasive tool in the form of at least one of alphanumeric information or graphic information overlaid on the image produced by said ultrasound.

19. The apparatus of claim 17, wherein said data processor is additionally programmed to calculate and display the expected trajectory of said medical invasive tool according to its bending.

20. The apparatus of claim 17, wherein said medical invasive tool is selected from the group comprising: needle, biopsy needle, ablation device.

21. The apparatus of claim 17, wherein at least one first position measuring component is attached at a known position on said medical invasive tool.

22. The apparatus of claim 17, wherein said articulated arm is attached at a known position to said medical invasive tool.

23. The apparatus of claim 17, wherein an at least one second position measuring component is attached at a known position to said ultrasound transducer.

24. The apparatus of claim 17, wherein said at least one first position measuring component includes one position measuring component and at least one second position measuring component includes one position measuring component.

25. The apparatus of claim 18, wherein said articulated arm is attached at a known position to said ultrasound transducer.

26. The apparatus of claim 17, wherein said position measuring system is selected from the group comprising: magnetic, optic, acoustic, mechanical, inertial, or combinations thereof.

27. The apparatus of claim 17, wherein said position measuring system is magnetic.

28. The apparatus of claim 17, wherein said data processor is additionally programmed to enhance the echo of said invasive tool in an image to be displayed.

29. The apparatus of claim 28, wherein said data processor is additionally programmed to enhance the echo of said invasive tool based on said identification of echo points or echo segments.

30. The apparatus of claim 28, wherein said data processor is additionally programmed to enhance the echo of said invasive tool by applying local image processing tools based on said calculation of the relative position or velocity of said invasive tool with respect to said ultrasound transducer.

* * * * *